(12) United States Patent
McGowan et al.

(10) Patent No.: US 10,259,793 B2
(45) Date of Patent: *Apr. 16, 2019

(54) 2-AMINOPYRIMIDINE DERIVATIVES FOR THE TREATMENT OF VIRAL INFECTIONS

(71) Applicant: Janssen Sciences Ireland UC, Little Island, Co Cork (IE)

(72) Inventors: David Craig McGowan, Brussels (BE); Pierre Jean-Marie Bernard Raboisson, Rosieres (BE); Tim Hugo Maria Jonckers, Heist-op-den-Berg (BE)

(73) Assignee: Janssen Sciences Ireland UC, Little Island, Co Cork (IE)

(*) Notice: Subject to any disclaimer, the term of this patent is extended or adjusted under 35 U.S.C. 154(b) by 0 days.

This patent is subject to a terminal disclaimer.

(21) Appl. No.: 15/464,050

(22) Filed: Mar. 20, 2017

(65) Prior Publication Data

US 2017/0342035 A1 Nov. 30, 2017

Related U.S. Application Data

(63) Continuation of application No. 14/769,773, filed as application No. PCT/EP2014/053273 on Feb. 20, 2014, now Pat. No. 9,598,378.

(30) Foreign Application Priority Data

Feb. 21, 2013 (EP) .................................. 13156167

(51) Int. Cl.
 *C07D 239/47* (2006.01)
 *A61K 31/505* (2006.01)
 *C07D 239/48* (2006.01)

(52) U.S. Cl.
 CPC .......... *C07D 239/47* (2013.01); *A61K 31/505* (2013.01); *C07D 239/48* (2013.01)

(58) Field of Classification Search
 CPC ... C07D 239/47; C07D 239/48; A61K 31/505
 USPC ......................................... 544/298; 514/272
 See application file for complete search history.

(56) References Cited

U.S. PATENT DOCUMENTS

| | | | |
|---|---|---|---|
| 6,028,076 A | 2/2000 | Hirota et al. | |
| 6,329,381 B1 | 12/2001 | Kurimoto et al. | |
| 6,376,501 B1 | 4/2002 | Isobe et al. | |
| 6,458,798 B1 | 10/2002 | Fujita et al. | |
| 6,503,908 B1 | 1/2003 | Maw | |
| 6,583,148 B1 | 6/2003 | Kelley et al. | |
| 6,951,866 B2 | 10/2005 | Fujita et al. | |
| 7,030,118 B2 | 4/2006 | Lombardo et al. | |
| 7,091,232 B2 | 8/2006 | Chow et al. | |
| 7,498,409 B2 | 3/2009 | Vlach et al. | |
| 7,524,852 B2 | 4/2009 | Arai et al. | |
| 7,531,547 B2 | 5/2009 | Dillon et al. | |
| 7,754,728 B2 | 7/2010 | Isobe et al. | |
| 7,923,554 B2 | 4/2011 | Hoornaert et al. | |
| 8,012,964 B2 | 9/2011 | Kurimoto et al. | |
| 8,022,077 B2 | 9/2011 | Simmen et al. | |
| 8,455,458 B2 | 6/2013 | Marcum et al. | |
| 8,486,952 B2 | 7/2013 | Boy et al. | |
| 8,637,525 B2 | 1/2014 | Boy et al. | |
| 8,916,575 B2 | 12/2014 | McGowan et al. | |
| 9,133,192 B2 | 9/2015 | McGowan et al. | |
| 9,284,304 B2 | 3/2016 | McGowan et al. | |
| 9,365,571 B2 | 6/2016 | McGowan et al. | |
| 9,376,448 B2 | 6/2016 | Charifson et al. | |
| 9,416,114 B2 | 8/2016 | Gembus et al. | |
| 9,422,250 B2 | 8/2016 | McGowan | |
| 9,499,549 B2 | 11/2016 | McGowan et al. | |
| 9,556,176 B2 | 1/2017 | Bonfanti et al. | |
| 9,556,199 B2 | 1/2017 | McGowan et al. | |
| 9,598,378 B2 * | 3/2017 | McGowan | C07D 239/48 |
| 9,663,474 B2 | 5/2017 | Last et al. | |
| 9,878,996 B2 | 1/2018 | Silverman et al. | |
| 2005/0054590 A1 | 3/2005 | Averett | |
| 2006/0258682 A1 | 11/2006 | Liao et al. | |
| 2007/0225303 A1 | 9/2007 | Ogita et al. | |
| 2009/0285782 A1 | 11/2009 | Gao et al. | |
| 2010/0143299 A1 | 6/2010 | Gao et al. | |
| 2014/0148433 A1 | 5/2014 | Follmann et al. | |
| 2015/0274676 A1 | 10/2015 | McGowan et al. | |
| 2015/0299221 A1 | 10/2015 | Bonfanti et al. | |
| 2015/0336907 A1 | 11/2015 | Gembus et al. | |
| 2016/0304531 A1 | 10/2016 | Bonfanti et al. | |
| 2017/0349557 A1 | 12/2017 | Last et al. | |

FOREIGN PATENT DOCUMENTS

| | | |
|---|---|---|
| CN | 101784548 A | 7/2010 |
| EP | 0882727 | 12/1998 |
| EP | 0899263 A3 | 3/1999 |
| EP | 1552842 A1 | 6/2003 |
| EP | 1110951 A1 | 6/2006 |
| EP | 1939198 A1 | 7/2008 |
| EP | 1970373 A1 | 9/2008 |
| EP | 2133353 A1 | 12/2009 |
| EP | 2138497 A1 | 12/2009 |
| JP | 64063582 | 3/1989 |
| JP | 2000053653 | 2/2000 |
| JP | 2000053654 | 2/2000 |
| JP | 2008222557 A | 9/2008 |
| JP | 2009528989 A | 8/2009 |
| JP | 2010522151 A | 7/2010 |
| JP | 2010532353 A | 10/2010 |
| WO | 199801448 A1 | 1/1998 |
| WO | 199808847 A1 | 3/1998 |
| WO | 199814448 A1 | 4/1998 |
| WO | 199850370 A1 | 11/1998 |
| WO | 199928321 A1 | 6/1999 |
| WO | 199932122 A1 | 7/1999 |
| WO | 199940091 A1 | 8/1999 |
| WO | 199941253 A1 | 8/1999 |

(Continued)

OTHER PUBLICATIONS

Abdillahi, et al., "Synthesis of a Novel Series of Thieno[3,2-d]pyrimidin-4-(3H)-ones", Synthesis, vol. 9: pp. 1428-1430 (2010).

(Continued)

*Primary Examiner* — Deepak R Rao

(57) ABSTRACT

This invention relates to 2-aminopyrimidine derivatives, processes for their preparation, pharmaceutical compositions, and their use in treating viral infections.

6 Claims, No Drawings

Specification includes a Sequence Listing.

(56) References Cited

FOREIGN PATENT DOCUMENTS

| | | |
|---|---|---|
| WO | 200006577 A1 | 2/2000 |
| WO | 200061562 A1 | 10/2000 |
| WO | 2002087513 A2 | 11/2002 |
| WO | 2002088080 A2 | 11/2002 |
| WO | 2003055890 A1 | 7/2003 |
| WO | 2004029054 A1 | 8/2004 |
| WO | 2005007672 A2 | 1/2005 |
| WO | 2005092892 A1 | 10/2005 |
| WO | 2005092893 A1 | 10/2005 |
| WO | 2006015985 A1 | 2/2006 |
| WO | 2006050843 A1 | 5/2006 |
| WO | 2006117670 A1 | 11/2006 |
| WO | 2006120252 A2 | 11/2006 |
| WO | 2007034881 A1 | 3/2007 |
| WO | 2007056208 A1 | 5/2007 |
| WO | 2007063934 A1 | 6/2007 |
| WO | 2007084413 A2 | 7/2007 |
| WO | 2007093901 A1 | 8/2007 |
| WO | 2008009078 A2 | 1/2008 |
| WO | 2008073785 A2 | 6/2008 |
| WO | 2008075103 A1 | 6/2008 |
| WO | 2008114008 A1 | 9/2008 |
| WO | 2008114817 A1 | 9/2008 |
| WO | 2008114819 A1 | 9/2008 |
| WO | 2008115319 A2 | 9/2008 |
| WO | 2008147697 A1 | 12/2008 |
| WO | 2009005687 A1 | 1/2009 |
| WO | 2009023179 A2 | 2/2009 |
| WO | 2009030998 A1 | 3/2009 |
| WO | 2009067081 A1 | 5/2009 |
| WO | 2009080836 A2 | 7/2009 |
| WO | 2009099650 A2 | 8/2009 |
| WO | WO2009032668 A3 | 9/2009 |
| WO | 2009134624 A1 | 11/2009 |
| WO | 2010006025 A1 | 1/2010 |
| WO | 2010007116 A3 | 1/2010 |
| WO | 2011014535 A1 | 2/2011 |
| WO | 2011049825 A1 | 4/2011 |
| WO | 2011049987 | 4/2011 |
| WO | 2011062253 A1 | 5/2011 |
| WO | 2011062372 A3 | 5/2011 |
| WO | 2012066335 A1 | 5/2012 |
| WO | 2012067269 A1 | 5/2012 |
| WO | 2012156498 A1 | 11/2012 |
| WO | 2013068438 A1 | 5/2013 |
| WO | 2013117615 A1 | 8/2013 |
| WO | 2014053595 A1 | 4/2014 |

OTHER PUBLICATIONS

Banker (Editor), "Prodrugs", Modem Pharmaceutics, Third Edition: pp. 596 (1976).
Baraldi, et al., "New Strategies for the Synthesis of A3 Adenosine Receptor Antagonists", Bioorganic & Medicinal Chemistry, vol. 11: pp. 4161-4169 (2003).
Barker, et al., "A Rapid Conversion of 3-Oxothiolanes into 3-Aminothiophenes", Synthetic Communications, vol. 32(16): pp. 2565-2568 (2002).
Bell, et al., "Chemistry of 5-Pyrimidinecarboxaldehydes", Journal of Heterocyclic Chemistry, vol. 29: pp. 41-44 ( Jan.-Feb. 1983).
Bennet, et al. (Editor), "Part XIV Oncology", Cecil Textbook of Medicine,vol. 1, 20th Edition: pp. 1004-1010 (1996).
Bizanek, et al., Isolation and Structure of an Intrastrand Cross-Link Adduct of Mitomycin C nd DNA, Biochemistry, 1992, pp. 3084-3091, vol. 31.
Brittain et al., "Effects of Pharmaceutical Processing on Drug Polymorphs and Solvates", Polymorphism in Pharmaceutical Solids, 1999, pp. 331-360, Chapter 8.
Bruns, et al, "Solubilities of Adenosine Antagonists Determined by Radioreceptor Assay", Journal of Pharmacy and Pharmacology, vol. 41: pp. 590-594 (1989).
Chawla, et al., "Challenges in Polymorphism of Pharmaceuticals", Current Research & Information on Pharmaceutical Sciences, vol. 5(1): pp. 9-12 ( Jan.-Mar. 2004).
De Clercq, et al., "(S)-9-(2,3-Dihydroxypropyl)adenine: An Aliphatic Nucleoside Analaog with Broad-Spectrum Antiviral Activity", Science, 1978, pp. 563-565, vol. 200.
Dermer, "Another Anniversary for the War on Cancer", Bio/Technology, vol. 12: pp. 320 (Mar. 1994).
Freshney, et al., Culture of Animal Cells, Manual of Basic Technique, 1983, pp. 1-6, Chapter 1.
Fried, et al., "Peginterferon Alfa-2a Plus Ribavirin for Chronic Hepatitis C Virus Infection", New England Journal of Medicine, Sep. 26, 2002, pp. 975-985, vol. 347 (13).
Grimm, et al., "Toll-like receptor (TLR) 7 and TLR8 expression on CD133+ cells in colorectal cancer points to a specific rold for inflammation inducted TLRs in tumourigenesis and tumour progression", European Journal of Cancer, 2010, pp. 2849-2857, vol. 46.
Hackam, et al, "Translation of Research Evidence From animals to Humans", JAMA, vol. 296 (14): pp. 1731-1732 (2006).
Hoffmann, "The Immune Response of *Drosophila*", Nature, vol. 426: pp. 33-38 (Nov. 6, 2003).
Hood, et al., "Immunoprofiling toll-like receptor ligands Comparison of Immunostimulatory and proinflammatory profiles in ex vivo human blood models", Human Vaccines, vol. 6(4): pp. 322-335 (Apr. 2010).
Horscroft, et al., "Antiviral applications of toll-like receptor agonists", J. Antimicrob. Chemother., pp. 1-13 (Jan. 18, 2016).
Huddleston, et al., "A Convenient Synthesis of 2-Substituted 3-Hydroxy- and 3-Amino-Thiophens From Derivatives of 2-Choroacrylic Acid", Synthetic Communications, vol. 9(8): pp. 731-734 (1979).
Isobe, et al., "Synthesis and Structure-Activity Relationships of 2-Substituted-8-hydroxyadenine Derivatives as Orally Available Interferon Inducers without Emetic Side Effects", Bioorganic & Medicinal Chemistry, vol. 11: pp. 3641-3647, (2003).
Jiang, et al., "Synthesis of 4-chlorothieno[3,2-d]pyrimidine", Chemical Industry and Engineering Progress, vol. 30: pp. 2532-2535, (2011). [With English Abstract].
Jordan, "Tamoxifen: A Most Unlikely Pioneering Medicine", Nature Reviews, vol. 2: pp. 205-213, (Mar. 2003).
Kanzler, et al., "Therapeutic Targeting of Innate Immunity with Toll-Like Receptor Agonists and Antagonists", Nature Medicine, vol. 13(5): pp. 552-559 (May 2007).
Krieger, et al, Enhancement of Hepatitis C Virus RNA Replication by Cell Culture, Journal of Virology, May 1, 2001, 4614-1624, 75-10, DE.
Kurimoto, et al., "Synthesis and Structure—Activity Relationships of 2-Amino-8-hydroxyadenines as Orally Active Interferon Inducing Agents", Bioorganic & Medicinal Chemistry, vol. 11: pp. 5501-5508 (2003).
Liu et al., "Synthesis and Biological Activity of 3- and 5-Amino Derivatives of Pyridine-2Carboxaldehyde Thiosemicarbazone", J. Med. Chem, Vo. 39: pp. 2586-2593 (1996).
Lohmann et al., Viral and Cellular Determinants of Hepatitis C Virus RNA Replication in Cell Culture, Journal of Virology, Mar. 2003, pp. 3007-3019, vol. 77, No. 5.
Lohmann, et al., Replication of Subgenomic Hepatitis C Virus RNAs in a Hepatoma Cell Line, Science, 1999, pp. 110-113, vol. 285.
Makkouk et al., "The potential use of Toll-Like Receptors (TLR) agonistd and antagonists as prophylactic and/or therapeutic agents", Immunopharmacology and Immunotoxicology, vol. 31(3): pp. 331-338 (2009).
McGowan et al., "Novel Pyrimidine Toll-Like Receptor 7 and 8 Dual Agonists to Treat Hepatitis B Virus", Journal of Medicinal Chemistry, 2016, pp. 7936-7949, vol. 59 No. 17.
Mesguiche, et al., "4-Alkoxy-2,6-diaminopyrimidine Derivatives: Inhibitors of Cyclin Dependent Kinases 1 and 2", Boorganic & Medicinal Chemistry Letters, vol. 13: pp. 217-222 (2003).
Moreau, et al., "Synthesis of cyclic adenosine 5'-diphosphate ribose analogues: a C2' endo/syn "southern" ribose conformation underlies activity at the sea urchin cADPR receptor", Organic & Biomolecular Chemistry, vol. 9: pp. 278-290 (2011).

(56) References Cited

OTHER PUBLICATIONS

Musmuca, et al., "Small-Molecule interferon Inducers. Toward the Comprehension of the Molecular Determinants through Ligand-Based Approaches", J. Chem. Inf. Model., vol. 49: pp. 1777-1786 (2009).

Newman, et al., "Solid-State Analysis of the Active Pharmaceutical Ingredient in Drug Products", Drug Discovery Today, Oct. 19, 2003, pp. 898-905, vol. 8(19).

O'Ohara, et al., "Regioselective Synthesis of Imidazo[4,5-g]quinazoline Quinone Nucleosides and Quinazoline Amino Nucleosides. Studies of their Xanthine Oxidase and Purine Nucleoside Phosphorylase Substrate Activity", J. Org. Chem. vol. 56: pp. 776-785 (1991).

Ohto, et al., "Structure and Function of Toll-Like Receptor 8", Microbes and Infections, vol. 16: pp. 273-282 (2014).

Organic Syntheses Collective, "3-Methylcoumarone", Organic Syntheses Collective, 1963, pp. 43-46, vol. 4.

Takeda, et al. "Toll-Like Receptors", Annu. Rev. Immunol, vol. 21: pp. 335-376 (2003).

Thomas, et al., "Investigating Toll-Like Receptor Agonists for Potential to Treat Hepatitis C Virus Infection", Antimicrobial Agents and Chemotherapy, vol. 51(8): pp. 2969-2978 (Aug. 2007).

Tomonori, et al., "Ti-Crossed-Claisen Condensation between Carboxylic Ester and Acid Chlorides or Acids: A Highly Selective and General Method for the Preparation of Various β-Keto Esters", Journal of the American Chemical Society, vol. 127:pp. 2854-2855 (2005).

Tran, et al, "Design and optimization of orally active TLR7 agonists for the treatment of hepatitis C virus infection", Bioorganic & Medicinal Chemistry Letters, vol. 21: pp. 2389-2393 (2011).

Ulevitch, "Therapeutics Targeting the Innate Immune System", Nature, vol. 4: pp. 512-520 (Jul. 2004).

Vedantham, et al., "Mechanism of Interferon Action in Hairy Cell Leukemia: A Model of Effective Cancer Biotherapy", Cancer Research, vol. 52: pp. 1056-1066 (Mar. 1, 1992).

Warshakoon, et al., "Potential Adjuvantic Properties of Innate Immune Stimuli", Human Vaccines, vol. 5(6): pp. 381-394 (Jun. 2009).

Wermuth, "Molecular Variations Based on Isosteric Replacements", The Practice of Medicinal Chemistry, 1996, pp. 203-237, Ch. 13.

Wolff, et al, Burger's Medicinal Chemistry and Drug Discovery, -, 1994, pp. 975-977, 5th Edition, vol. 1.

Yin, et al., "Synthesis of 2,4-Diaminoquinazolines and Tricyclic Quinazolines by Cascade Reductive Cyclization of Methyl N-Cyano-2-nitrobenzimidates", J. Org. Chem., vol. 77: pp. 2649-2658 (2012).

Yu, et al, "Toll-Like Receptor 7 Agonists: Chemical Feature Based", Plos One, vol. 8 (3): pp. 1-11 e56514, (Mar. 20, 2013).

Yu, et al., "Dual Character of Toll-Like Receptor Signaling: Pro-Tumorigenic Effects and Anti-Tumor Functions", Biochimica et Biophysica Acta, vol. 1835: pp. 144-154 (2013).

Zhao, et al, "Toll-Like Receptors and Prostate Cancer", Frontiers in Immunology, vol. 5 (Article 352): pp. 1-7 (Jul. 2014).

Isobe, et al, "Synthesis and Biological Evaluation of Novel 9-Substituted-8-Hydroxyadenine Derivatives as Potent Inferferon Inducers", J. Med. Chem., vol. 49; pp. 2088-2095 (2006).

Jurk, et al., "Human TLR7 or TLR8 Independently Confer Responsiveness to the Antiviral Compound R-848", Nature Immunology, Jun. 2002, pp. 499, vol. 3 (6).

Kurimoto, et al., "Synthesis and Evaluation of 2-Substituted 8-Hydroxyadenines as Potent Interferon Inducers wit Improved Oral Bioavailabilities", Bioorganic & Medicinal Chemistry, vol. 12; pp. 1091-1099 (2004).

Lee, et al., "Activation of Anti-Hepatitis C Virus Responses via Toll-Like Receptor 7", PNAS, vol. 3 (6); pp. 1828-1833 (Feb. 7, 2006).

Roethle, et al., "Identification and Optimization of Pteridinone Toll-Like Receptor 7 (TLR7) Agonists for the Oral Treatment of Viral Hepatitis", Journal of Medicinal Chemistry, vol. 56; pp. 7324-73333 (2013).

\* cited by examiner

SEQUENCE LISTING

```
<160> NUMBER OF SEQ ID NOS: 1

<210> SEQ ID NO 1
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gaaactgaaa ct                                                        12
```

2-AMINOPYRIMIDINE DERIVATIVES FOR THE TREATMENT OF VIRAL INFECTIONS

CROSS-REFERENCE TO RELATED APPLICATIONS

This application is a continuation of U.S. patent application Ser. No. 14/769,773 filed on Aug. 21, 2015, which is a national phase entry of International Application No. PCT/EP2014/053273, filed on Feb. 20, 2014, which claims priority to EP Patent Application No. 13156167.2, filed on Feb. 21, 2013, each of which is incorporated herein in its entirety.

SEQUENCE LISTING

The instant application contains a Sequence Listing which has been submitted electronically in ASCII format and is hereby incorporated by reference in its entirety. Said ASCII copy, created on Mar. 13, 2017, is named TIP0291USCNT1_SL.txt and is 217 bytes in size.

This invention relates to 2-aminopyrimidine derivatives, processes for their preparation, pharmaceutical compositions, and their use in treating viral infections.

The present invention relates to the use of 2-aminopyrimidine derivatives in the treatment of viral infections, immune or inflammatory disorders, whereby the modulation, or agonism, of toll-like-receptors (TLRs) is involved. Toll-Like Receptors are primary transmembrane proteins characterized by an extracellular leucine rich domain and a cytoplasmic extension that contains a conserved region. The innate immune system can recognize pathogen-associated molecular patterns via these TLRs expressed on the cell surface of certain types of immune cells. Recognition of foreign pathogens activates the production of cytokines and upregulation of co-stimulatory molecules on phagocytes. This leads to the modulation of T cell behaviour.

It has been estimated that most mammalian species have between ten and fifteen types of Toll-like receptors. Thirteen TLRs (named TLR1 to TLR13) have been identified in humans and mice together, and equivalent forms of many of these have been found in other mammalian species. However, equivalents of certain TLR found in humans are not present in all mammals. For example, a gene coding for a protein analogous to TLR10 in humans is present in mice, but appears to have been damaged at some point in the past by a retrovirus. On the other hand, mice express TLRs 11, 12, and 13, none of which are represented in humans. Other mammals may express TLRs which are not found in humans. Other non-mammalian species may have TLRs distinct from mammals, as demonstrated by TLR14, which is found in the Takifugu pufferfish. This may complicate the process of using experimental animals as models of human innate immunity.

For reviews on TLRs see the following journal articles. Hoffmann, J. A., Nature, 426, p 33-38, 2003; Akira, S., Takeda, K., and Kaisho, T., Annual Rev. Immunology, 21, p 335-376, 2003; Ulevitch, R. J., Nature Reviews: Immunology, 4, p 512-520, 2004.

Compounds indicating activity on Toll-Like receptors have been previously described such as purine derivatives in WO 2006/117670, adenine derivatives in WO 98/01448 and WO 99/28321, and pyrimidines in WO 2009/067081.

However, there exists a strong need for novel Toll-Like receptor modulators having preferred selectivity, higher potency, higher metabolic stability, and an improved safety profile compared to the compounds of the prior art.

In accordance with the present invention a compound of formula (I) is provided

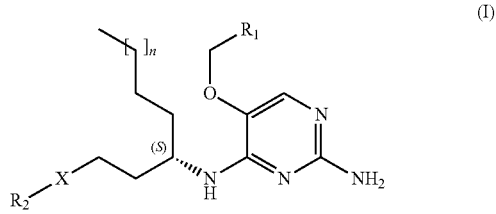

or a pharmaceutically acceptable salt, tautomer(s), stereo-isomeric forms, solvate or polymorph thereof, wherein
X represents S, S=O or O=S=O,
$R_1$ is hydrogen, $(C_{1-6})$-alkyl, $(C_{1-6})$-alkoxy or aryl,
$R_2$ is $(C_{1-3})$-alkyl or $(C_{3-6})$-cycloalkyl and
n=1 or 2.

The compounds of formula (I) and their pharmaceutically acceptable salts, tautomer(s), stereo-isomeric forms, solvate or polymorph thereof have activity as pharmaceuticals, in particular as modulators of Toll-Like Receptors (especially TLR7 and/or TLR8 activity).

In a further aspect the present invention provides a pharmaceutical composition comprising a compound of formula (I) or a pharmaceutically acceptable salt, tautomer, stereo-isomeric form, solvate or polymorph thereof together with one or more pharmaceutically acceptable excipients, diluents or carriers.

Furthermore a compound of formula (I) or a pharmaceutically acceptable salt, solvate, tautomer, stereo-isomeric form or polymorph thereof according to the current invention, or a pharmaceutical composition comprising said compound of formula (I) or a pharmaceutically acceptable salt, solvate, tautomer, stereo-isomeric form or polymorph thereof can be used as a medicament.

Another aspect of the invention is that a compound of formula (I) or its pharmaceutically acceptable salt, solvate, tautomer, stereo-isomeric form or polymorph thereof, or said pharmaceutical composition comprising said compound of formula (I) or a pharmaceutically acceptable salt, solvate, tautomer, stereo-isomeric form or polymorph thereof can be used accordingly in the treatment of a disorder where the modulation of TLR's, more specifically TLR7 and/or TLR8, is involved.

The term "$(C_{1-6})$-alkyl" or "$(C_{1-3})$-alkyl" refers to a straight-chain, branched-chain or cyclic saturated aliphatic hydrocarbon containing the specified number of carbon atoms.

The term "aryl" means an aromatic ring structure optionally comprising one or two heteroatoms selected from N, O and S, in particular from N and O. Said aromatic ring structure may have 4, 5, 6 or 7 ring atoms. In particular, said aromatic ring structure may have 5 or 6 ring atoms.

The term "$(C_{1-6})$-alkoxy refers to an alkyl (carbon and hydrogen chain) group singular bonded to oxygen like for instance a methoxy group or ethoxy group.

The term "$(C_{3-6})$-cycloalkyl" means refers to a carbocyclic ring containing the specified number of carbon atoms.

As used herein, any chemical formula with bonds shown only as solid lines and not as solid wedged or hashed wedged bonds, or otherwise indicated as having a particular configuration (e.g. R, S) around one or more atoms, contemplates each possible stereoisomer, or mixture of two or more stereoisomers.

The terms "stereoisomers", "stereoisomeric forms" or "stereochemically isomeric forms" hereinbefore or hereinafter are used interchangeably.

The invention includes all stereoisomers of the compounds of the invention either as a pure stereoisomer or as a mixture of two or more stereoisomers.

Enantiomers are stereoisomers that are non-superimposable mirror images of each other. A 1:1 mixture of a pair of enantiomers is a racemate or racemic mixture.

Diastereomers (or diastereoisomers) are stereoisomers that are not enantiomers, i.e. they are not related as mirror images. If a compound contains a double bond, the substituents may be in the E or the Z configuration. If a compound contains an at least disubstituted non-aromatic cyclic group, the substituents may be in the cis or trans configuration.

Therefore, the invention includes enantiomers, diastereomers, racemates, E isomers, Z isomers, cis isomers, trans isomers and mixtures thereof, whenever chemically possible.

The meaning of all those terms, i.e. enantiomers, diastereomers, racemates, E isomers, Z isomers, cis isomers, trans isomers and mixtures thereof are known to the skilled person.

The absolute configuration is specified according to the Cahn-Ingold-Prelog system. The configuration at an asymmetric atom is specified by either R or S. Resolved stereoisomers whose absolute configuration is not known can be designated by (+) or (−) depending on the direction in which they rotate plane polarized light. For instance, resolved enantiomers whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other stereoisomers. Thus, when a compound of Formula (I) is for instance specified as (R), this means that the compound is substantially free of the (S) isomer; when a compound of Formula (I) is for instance specified as E, this means that the compound is substantially free of the Z isomer; when a compound of Formula (I) is for instance specified as cis, this means that the compound is substantially free of the trans isomer.

Pharmaceutically acceptable salts of the compounds of formula (I) include the acid addition and base salts thereof. Suitable acid addition salts are formed from acids which form non-toxic salts. Suitable base salts are formed from bases which form non-toxic salts.

The compounds of the invention may also exist in unsolvated and solvated forms. The term "solvate" is used herein to describe a molecular complex comprising the compound of the invention and one or more pharmaceutically acceptable solvent molecules, for example, ethanol.

The term "polymorph" refers to the ability of the compound of the invention to exist in more than one form or crystal structure.

The compounds of the present invention may be administered as crystalline or amorphous products. They may be obtained for example as solid plugs, powders, or films by methods such as precipitation, crystallization, freeze drying, spray drying, or evaporative drying. They may be administered alone or in combination with one or more other compounds of the invention or in combination with one or more other drugs. Generally, they will be administered as a formulation in association with one or more pharmaceutically acceptable excipients. The term "excipient" is used herein to describe any ingredient other than the compound(s) of the invention. The choice of excipient depends largely on factors such as the particular mode of administration, the effect of the excipient on solubility and stability, and the nature of the dosage form.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, for example, for oral, rectal, or percutaneous administration. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions, and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. Also included are solid form preparations that can be converted, shortly before use, to liquid forms. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. The compounds of the present invention may also be administered via inhalation or insufflation by means of methods and formulations employed in the art for administration via this way. Thus, in general the compounds of the present invention may be administered to the lungs in the form of a solution, a suspension or a dry powder.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of infectious diseases will be able to determine the effective amount from the test results presented hereinafter. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight and general physical condition of the particular patient as well as other medication the individual may be taking, as is well known to those skilled in the art. Furthermore, it is evident that the effective amount may be lowered or increased depending on the response of the treated subject and/or depending on the evaluation of the physician prescribing the compounds of the instant invention. The effective amount ranges mentioned above are therefore only guidelines and are not intended to limit the scope or use of the invention to any extent.

Preparation of Compounds of Formula (I)

Overall scheme. Compound A was prepared according to procedures described in WO2008147697 and WO2009067081.

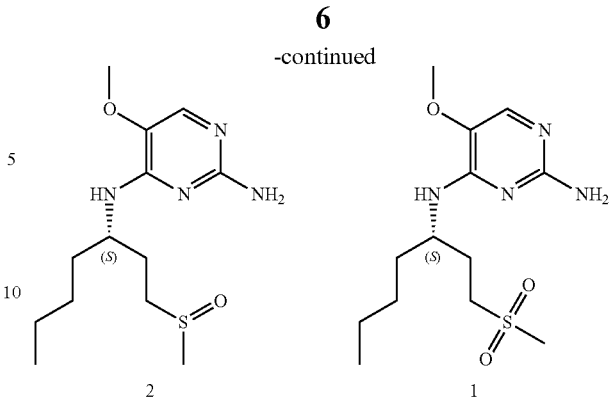

EXPERIMENTAL SECTION

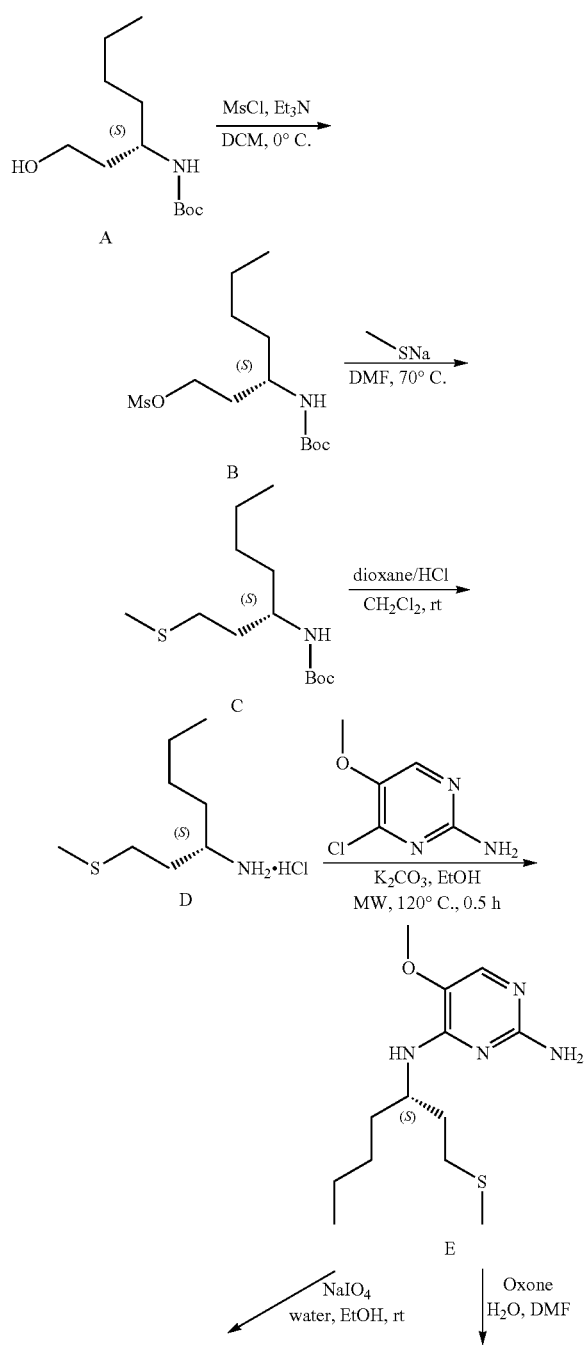

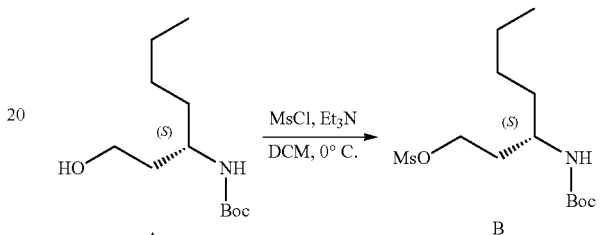

Triethylamine (10.5 g, 103.75 mmol, 2.4 eq.) was added to the solution of A (10 g, 43.23 mmol, 1 eq.) in $CH_2Cl_2$ (200 mL) at 0° C. Methanesulfonyl chloride (6.4 g, 55.87 mmol, 1.3 eq.) was added dropwise to the solution and stirred 1.5 hours at 0° C. $CH_2Cl_2$ (500 mL) was added. The solution was washed with aq. $NaHCO_3$, brine, and dried over $Na_2SO_4$, the solids were removed by filtration and the solvent of the filtrate was removed under reduced pressure to give B. Used as such without further purification.

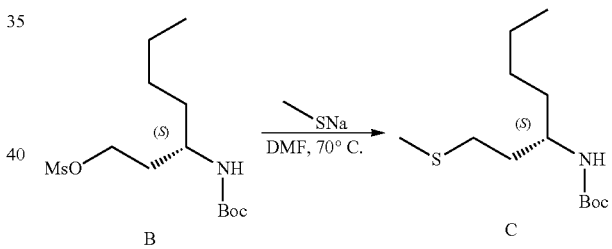

A mixture of B (12 g, 38.782 mmol, 1 eq.) and sodium thiomethoxide (4.08 g, 58.17 mmol, 1.5 eq.) in DMF (60 mL) was stirred overnight at 70° C. The solids were removed by filtration and the solvents of the filtrate were removed under reduced pressure. The crude was dissolved in ethyl acetate, washed with water, brine, dried over $Na_2SO_4$, the solids were removed by filtration and the solvents of the filtrate were removed under reduced pressure. The crude was purified by silica gel column chromatography (eluent: petroleum ether/ethyl acetate from 40/1 to 3/1) to afford C.

$^1$H NMR (400 MHz, chloroform-d) δ ppm 0.70-0.85 (m, 5H), 1.15-1.49 (m, 13H), 1.49-1.61 (m, 1H), 1.61-1.80 (m, 1H), 2.05 (s, 3H), 2.38-2.50 (m, 2H), 3.51 (br. s., 1H), 4.25 (br. s., 1H)

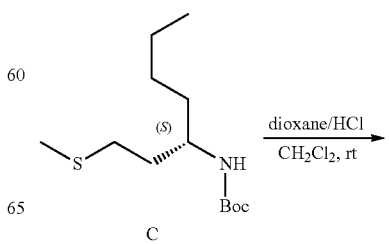

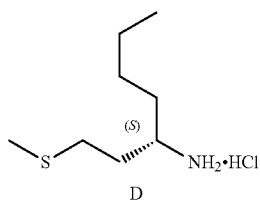

HCl/dioxane (47 mL, 187.43 mmol, 10 eq.) was added drop wise to a stirred solution of C (4.9 g, 18.74 mmol, 1 eq.) in CH$_2$Cl$_2$ at 0° C., and stirred for 1 hour at 25° C. The solution was concentrated under reduced pressure to give D. Used as such in the next step.

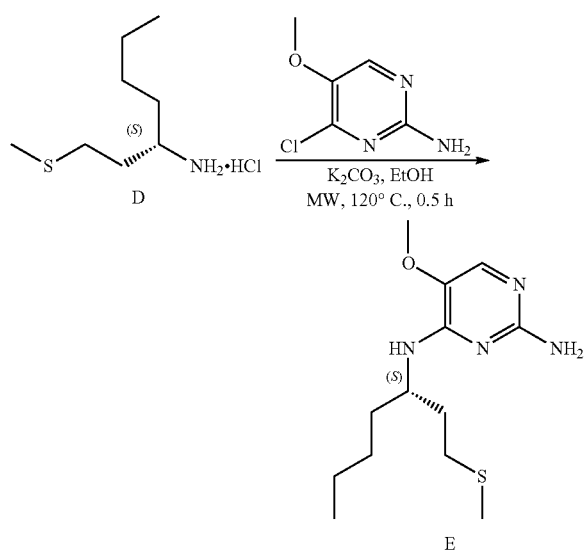

D (0.75 g, 3.79 mmol, 1 eq.), 2-amino-4-chloro-5-methoxypyrimidine (0.908 g, 5.69 mmol, 1.5 eq.) and K$_2$CO$_3$ (1.57 g 11.38 mmol, 3 eq.) were mixed in ethanol (20 mL). The mixture was stirred at 120° C. in the microwave for 30 minutes. The solvent was removed under reduced pressure. The crude was purified by preparative silica thin layer chromatography (eluent: CH$_2$Cl$_2$:CH$_3$OH=20:1) to afford E.
$^1$H NMR (400 MHz, chloroform-d) δ ppm 1.05-1.15 (m, 3H), 1.40-1.60 (m, 4H), 1.95 (m, 2H), 2.15 (m, 1H), 2.30 (d, 3H), 2.70 (t, 1H), 2.90 (t, 1H), 3.55 (m, 1H), 4.50 (m, 1H), 3.95 (s, 3H), 6.20 (d, 1H), 6.60 (br. s., 2H), 7.45 (s, 1H)

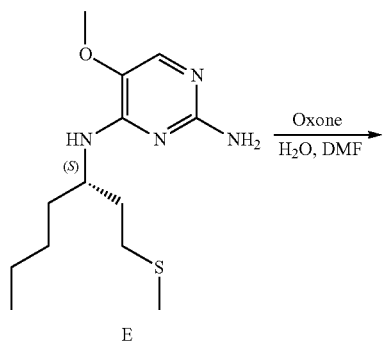

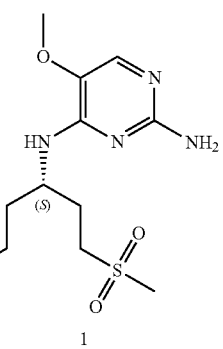

Oxone (6.959 g, 11.32 mmol, 3 eq.) was added to a solution of E (1.45 g, 3.773 mmol, 1 eq.) in DMF (100 mL) and water (100 mL). The mixture was stirred for 12 hours at 20° C. The solids were removed by filtration and the filtrate was basified to pH=8 with saturated, aq. Na$_2$CO$_3$ solution. The resultant mixture was concentrated under reduced pressure. The residue was purified by preparative high-performance liquid chromatography (column: gemini 150×30 mm×5 µm, C18, mobile phase: CH$_3$CN/water (0.05% HCl), Gradient: 2-32% CH$_3$CN, 0-8 min, flow rate: 30 mL/min). The best fractions were pooled and concentrated under reduced pressure to afford 1.
LC-MS 3.88 min
$^1$H NMR (400 MHz, methanol-d$_4$) δ ppm 0.92 (t, J=6.9 Hz, 3H), 1.21-1.50 (m, 4H), 1.69 (q, J=7.1 Hz, 2H), 1.95-2.28 (m, 2H), 2.98 (s, 3H), 3.09-3.22 (m, 2H), 3.87 (s, 3H), 4.37-4.55 (m, 1H), 7.26 (s, 1H) labile protons not observed.

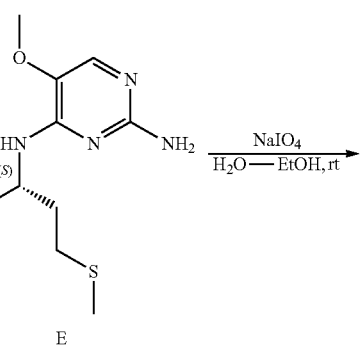

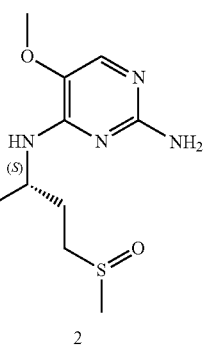

A solution of E (40 mg, 0.14 mmol, 1 eq.) in ethanol (40 mL) was treated with a solution of NaIO$_4$ (0.2 g, 1 mmol, 7.5 eq.) in water (10 mL), and then stirred at room temperature overnight. The solution was concentrated under vacuum. The residue was diluted with water and extracted with ethyl acetate. The combined organic layers were washed with brine, dried over $Na_2SO_4$, the solids were removed via filtration, and the solvent of the filtrate was removed under reduced pressure. The crude was purified by preparative high-performance liquid chromatography (C18 column, eluent: $CH_3CN$, $H_2O$ from 3/97 to 33/67, 0.05% NCI). The desired fractions were collected and concentrated under vacuum to afford 2.

LC-MS 3.78 min $^1$H NMR (400 MHz, methanol-$d_4$) δ ppm 0.90 (t, J=6.8 Hz, 3H), 1.19-1.49 (m, 4H), 1.67 (d, J=6.5 Hz, 2H), 1.91-2.15 (m, 2H), 2.63 (br. s., 3H), 2.69-2.96 (m, 2H), 3.85 (s, 3H), 4.46 (br. s., 1H), 7.25 (s, 1H) labile protons not observed.

LC-MS Analytical Method.

| Column | YMC-PACK ODS-AQ, 50 × 2.0 mm, 5 μm |
| --- | --- |
| Mobile Phase | A: $H_2O$ (0.1% TFA) |
| | B: acetonitrile (0.05% TFA) |

| TIME(min) | A % | B % |
| --- | --- | --- |
| 0 | 100 | 0 |
| 1 | 100 | 0 |
| 5 | 40 | 60 |
| 7.5 | 40 | 60 |
| 8 | 100 | 0 |

| Flow Rate | 0.8 mL/min |
| --- | --- |
| Wavelength | UV 220 nm |
| Column Temperature | 50° C. |
| MS polarity | positive |
| LCMS | Agilent 1100 |

Biological Activity of Compounds of Formula (I)
Description of Biological Assays
Assessment of TLR7 and TLR8 Activity The ability of compounds to activate human TLR7 and/or TLR8 was assessed in a cellular reporter assay using HEK293 cells transiently transfected with a TLR7 or TLR8 expression vector and NFκB-luc reporter construct.

Briefly, HEK293 cells were grown in culture medium (DMEM supplemented with 10% FCS and 2 mM Glutamine). For transfection of cells in 15 cm dishes, cells were detached with Trypsin-EDTA, transfected with a mix of CMV-TLR7 or TLR8 plasmid (1700 ng), NFκB-luc plasmid (850 ng) and a transfection reagent and incubated for 48 h at 37° C. in a humidified 5% $CO_2$ atmosphere. Transfected cells were then washed in PBS, detached with Trypsin-EDTA and resuspended in medium to a density of $1.25 \times 10^5$ cells/mL. Forty microliters of cells were then dispensed into each well in 384-well plates, where 200 nL of compound in 100% DMSO was already present. Following 6 hours incubation at 37° C., 5% $CO_2$, the luciferase activity was determined by adding 15 μL of Steady Lite Plus substrate (Perkin Elmer) to each well and readout performed on a ViewLux ultraHTS microplate imager (Perkin Elmer). Dose response curves were generated from measurements performed in quadruplicates. Lowest effective concentrations (LEC) values, defined as the concentration that induces an effect which is at least two fold above the standard deviation of the assay, were determined for each compound.

Compound toxicity was determined in parallel using a similar dilution series of compound with 40 μL per well of cells transfected with the CMV-TLR7 construct alone ($1.25 \times 10^5$ cells/mL), in 384-well plates. Cell viability was measured after 6 hours incubation at 37° C., 5% $CO_2$ by adding 15 μL of ATP lite (Perkin Elmer) per well and reading on a ViewLux ultraHTS microplate imager (Perkin Elmer). Data was reported as $CC_{50}$.

In parallel, a similar dilution series of compound was used (200 nL of compound in 100% DMSO) with 40 μL per well of cells transfected with NFκB-luc reporter construct alone ($1.25 \times 10^5$ cells/mL). Six hours after incubation at 37° C., 5% $CO_2$, the luciferase activity was determined by adding 15 μl of Steady Lite Plus substrate (Perkin Elmer) to each well and readout performed on a ViewLux ultraHTS microplate imager (Perkin Elmer). Counterscreen data is reported as LEC.

Activation of ISRE Promoter Elements

The potential of compounds to induce IFN-I was also evaluated by measuring the activation of interferon-stimulated responsive elements (ISRE) by conditioned media from PBMC. The ISRE element of sequence GAAACT-GAAACT (SEQ ID NO: 1) is highly responsive to the STAT1-STAT2-IRF9 transcription factor, activated upon binding of IFN-I to their receptor IFNAR (Clontech, PT3372-5W). The plasmid pISRE-Luc from Clontech (ref. 631913) contains 5 copies of this ISRE element, followed by the firefly luciferase ORF. A HEK293 cell line stably transfected with pISRE-Luc (HEK-ISREluc) was established to profile the conditioned PBMC cell culture media.

Briefly, PBMCs were prepared from buffy coats of at least two donors using a standard Ficoll centrifugation protocol. Isolated PBMCs were resuspended in RPMI medium supplemented with 10% human AB serum and $2 \times 10^5$ cells/well were dispensed into 384-well plates containing compounds (70 μL total volume).

After overnight incubation, 10 μL of supernatant was transferred to 384-well plates containing $5 \times 10^3$ HEK-ISRE-luc cells/well in 30 μL (plated the day before). Following 24 hours of incubation, activation of the ISRE elements was measured by assaying luciferase activity using 40 μL/well Steady Lite Plus substrate (Perkin Elmer) and measured with ViewLux ultraHTS microplate imager (Perkin Elmer). The stimulating activity of each compound on the HEK-ISREluc cells was reported as LEC value, defined as the compound concentration applied to the PBMCs resulting in a luciferase activity at least two fold above the standard deviation of the assay. The LEC in turn indicates the degree of ISRE activation on transfer of a defined amount of PBMC culture medium. Recombinant interferon α-2a (Roferon-A) was used as a standard control compound.

TABLE I

| | BIOLOGICAL ACTIVITY. | | |
| --- | --- | --- | --- |
| # | Human TLR 7 (LEC) μM | Human TLR 8 (LEC) μM | HEK-ISRE luc (LEC) μM |
| 1 | 2.0 | 1.7 | 0.65 |
| 2 | 1.4 | 9.2 | 4.8 |
| E | 3.9 | 10 | NA |

NA=not available. All compounds showed no toxicity up to the highest tested concentration. All compounds showed no activity (LEC>25 μM) in the HEK 293 NF-kB counterscreen assay described above.

The invention claimed is:

1. A compound of formula (I)

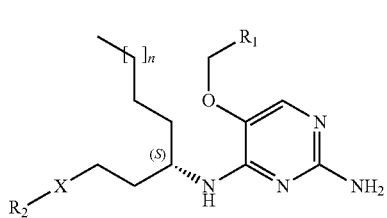

(I)

or a pharmaceutically acceptable salt, tautomer, stereoisomeric form or solvate thereof, wherein X represents S, S=O or O=S=O;
$R_1$ is H;
$R_2$ is $(C_{1-3})$-alkyl; and
n=1 or 2.

2. The compound of claim 1, wherein $R_2$ is methyl.

3. The compound of claim 1, wherein
$R_2$ is methyl
X is S; and
n is 1.

4. The compound of claim 1, wherein
$R_2$ is methyl;
X is S=O; and
n is 1.

5. The compound of claim 1, wherein
$R_2$ is methyl;
X is O=S=O; and
n is 1.

6. A pharmaceutical composition comprising a compound of claim 1, and at least one pharmaceutically acceptable excipient, diluent or carrier.

* * * * *